(12) United States Patent
Parto et al.

(10) Patent No.: US 10,285,583 B2
(45) Date of Patent: May 14, 2019

(54) SCANNING OPTICAL PROBE WITH FLEXING MECHANISM

(71) Applicant: Novartis AG, Basel (CH)

(72) Inventors: Kambiz Parto, Laguna Niguel, CA (US); Edouard G. Schmidtlin, San Francisco, CA (US); Barry L. Wheatley, Oceanside, CA (US)

(73) Assignee: Novartis AG, Basel (CH)

( * ) Notice: Subject to any disclaimer, the term of this patent is extended or adjusted under 35 U.S.C. 154(b) by 210 days.

(21) Appl. No.: 15/294,843

(22) Filed: Oct. 17, 2016

(65) Prior Publication Data

US 2018/0103842 A1  Apr. 19, 2018

(51) Int. Cl.
| | |
|---|---|
| *A61B 3/14* | (2006.01) |
| *A61B 3/10* | (2006.01) |
| *A61B 90/30* | (2016.01) |
| *A61B 3/12* | (2006.01) |
| *G02B 26/10* | (2006.01) |

(52) U.S. Cl.
CPC ............ *A61B 3/102* (2013.01); *A61B 3/1225* (2013.01); *A61B 3/14* (2013.01); *A61B 90/30* (2016.02); *G02B 26/103* (2013.01); *A61B 2090/306* (2016.02)

(58) Field of Classification Search
CPC ... A61B 5/0017; A61B 5/0031; A61B 5/0062; A61B 5/0066; A61B 5/0084; A61B 5/14514; A61B 5/14532; A61B 5/14546; A61B 5/14865; A61B 90/30; A61B 3/14; A61B 3/102; A61B 3/1225; A61B 1/07; A61B 1/00112; A61B 1/00172; A61B 1/00188; A61B 18/20; A61B 18/22; A61B 18/18; A61B 18/14; A61B 18/201; A61C 1/0046; A61C 19/06; A61C 5/40; G02B 26/103; G02B 6/00; G02B 7/00
USPC ................ 351/206, 218–225, 236, 243, 246; 600/104–108, 345, 347, 429, 478
See application file for complete search history.

(56) References Cited

U.S. PATENT DOCUMENTS

| | | |
|---|---|---|
| 2012/0310042 A1 | 12/2012 | Joos et al. |
| 2015/0080719 A1 | 3/2015 | Wheatley |
| 2015/0164311 A1* | 6/2015 | Yu ........................... A61B 1/07 600/478 |

* cited by examiner

*Primary Examiner* — Mustak Choudhury

(57) ABSTRACT

A scanning optical probe and method includes a cannula, optical fiber, lens, and an actuating mechanism for tilting the optical fiber back and forth within the cannula. An actuator in the probe handle is coupled to various flexing and guide components extending through the cannula and towards the distal end of the scanning optical probe. Reciprocating motion from the actuator is transmitted to the components thereby causing the optical fiber at the distal end of the scanning optical probe to aim across target surfaces. The light emitted from the optical fiber is processed to generate a scan of the target area.

17 Claims, 7 Drawing Sheets

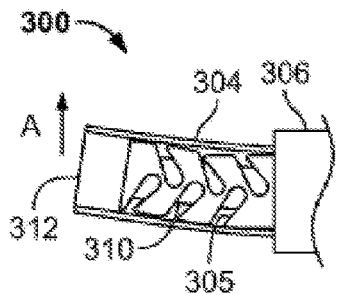 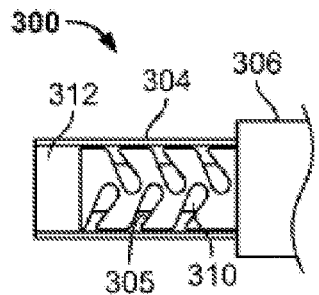 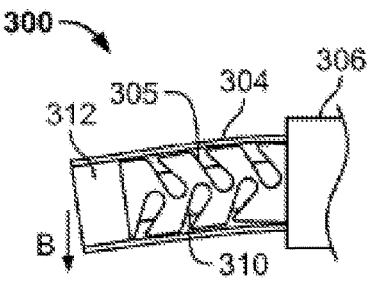
FIG. 6   FIG. 7   FIG. 8
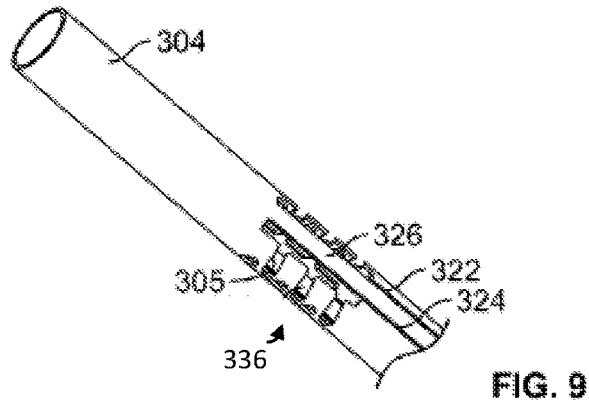
FIG. 9
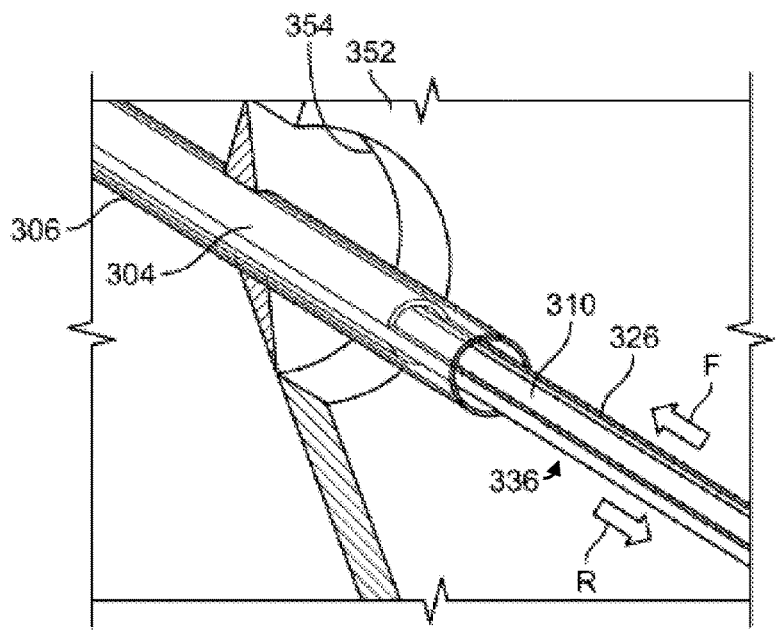
FIG. 10

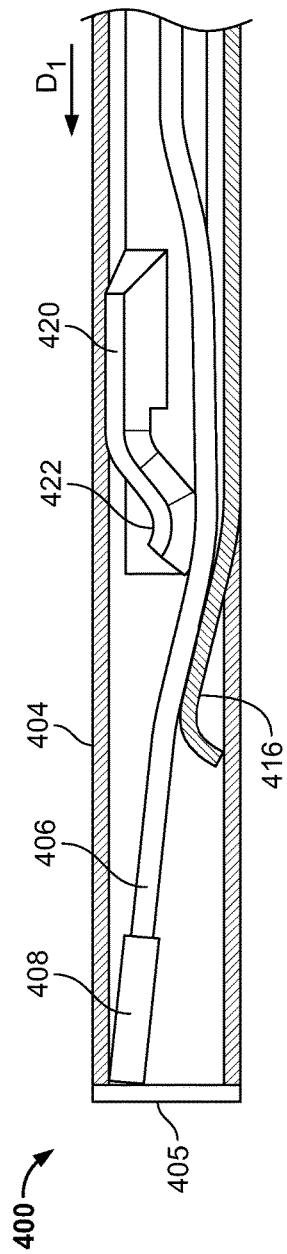 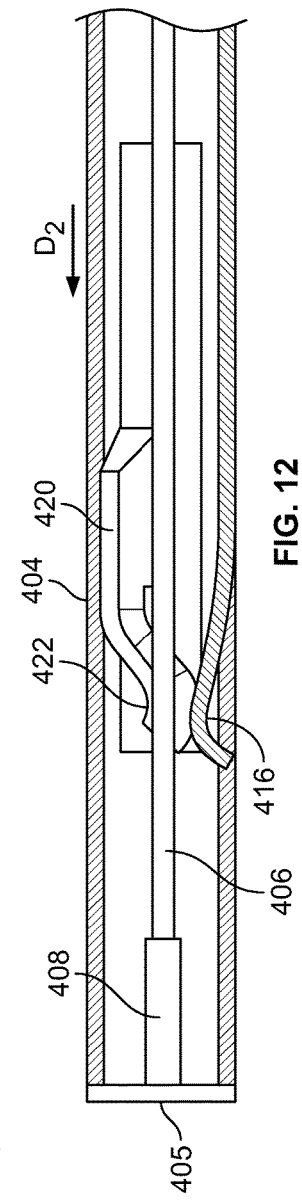 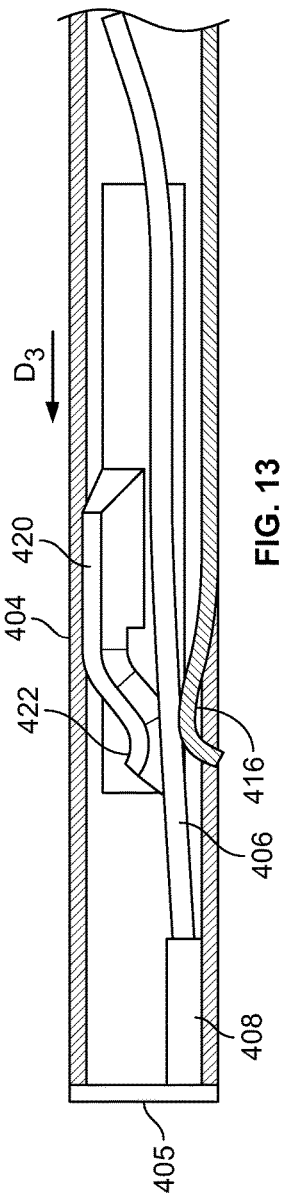

SCANNING OPTICAL PROBE WITH FLEXING MECHANISM

FIELD

The present disclosure relates generally surgical probes and, more particularly, to a scanning optical probe with flexing mechanism.

BACKGROUND

Widespread interest exists in obtaining high resolution imaging scans of anatomical targets. Desirable anatomical targets include, for example, the interior surfaces of the eye and vasculature.

One imaging technology capable of obtaining high resolution scans is optical coherence tomography (OCT). OCT technology obtains good depth resolution and need not contact the target surface to be interrogated.

OCT imaging technology has been incorporated into handheld optical probes. Such optical probes have been utilized to generate different types of scans of the target surface. An OCT image corresponding to a single point on the surface of the target is called an A-scan. An OCT image corresponding to traversing the imaging beam across a set of target points is typically referred to as a B-scan.

Despite the above mentioned OCT-based technologies, handheld scanning probes face a number of challenges. The challenges arise due to the nature of OCT image scanning which requires movement of the optical fiber with respect to the lens (or movement of the fiber/lens assembly together) to achieve the scan. In the microsurgical environment (e.g., ophthalmic applications) actuating the fiber or fiber/lens assembly is prohibited due to the lack of working space in the probe housing. The lack of working space arises due the relatively long length, small diameter, and rigidity of the probe housing. Consequently, motion of the fiber assembly is extremely restricted.

Accordingly, there is a need for scanning optical probes and methods that overcome the above mentioned challenges.

SUMMARY

A scanning optical probe and method includes a cannula, optical fiber, lens, and an actuating mechanism to deflect the distal end of the fiber. In embodiments, the actuating mechanism includes an actuator and an elongate support member coupled to the actuator and extending through the cannula to the distal end of the probe. When the elongate support member is activated, the distal end of the fiber is deflected back and forth, causing the light beam from the optical fiber to move across the target surface as desired.

In embodiments, the elongate support member includes a discrete predefined flexing region. The flexing region includes a plurality of slots in the side wall of the flexible member. Pull rods extend proximally from the flexing region to a probe handle. When the rods are reciprocally actuated, the end of the scanning optical probe is tilted back and forth.

In another embodiment, the actuating mechanism includes at least one guide which urges or biases the optical fiber to aim in a first direction. When the guides are moved, the optical fiber is repositioned to aim in a second direction.

An actuator in the probe handle can be linked to the guide. Reciprocating motion from the actuator is transmitted through the various components, causing the optical fiber at the distal end of the probe to tilt back and forth. The beam emitted from the fiber is processed to generate a scan of a target area.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 6-8 are side views of a distal section of a scanning optical probe shown moving in sequence from a first position to a second position;

FIG. 9 is a perspective view of a component of the scanning optical probe shown in FIGS. 6-8;

FIG. 10 is a partial perspective view of the proximal section of the scanning optical probe shown in FIGS. 6-8;

FIGS. 11-13 are cross sectional views of a distal section of another scanning optical probe wherein the optical fiber is shown moving in sequence from a first position to the second position;

DETAILED DESCRIPTION

The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein. All patents and publications recited herein are incorporated by reference in their entirety.

Figure 1A:
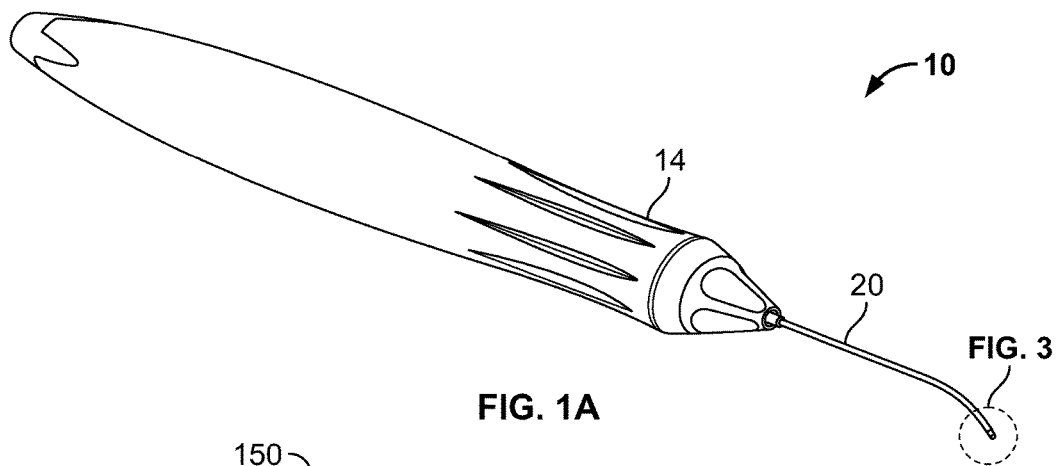
FIG. 1A is a perspective view of a scanning optical probe in accordance with an embodiment of the present invention.

FIG. 1A depicts a scanning optical probe 10 including a handle 14 and a cannula 20 extending distally from the handle.

The cannula 20 or equivalent type of housing structure is shown having a tubular shape and includes one bend. However, the cannula can have additional bends or be straight. Indeed, the shape and size of the cannula or housing may vary. For example, the inner diameter (ID) may range from 0.25 to 0.6 mm, and in embodiments is about 0.4 mm. The outer diameter (OD) may range from 0.4 to 1 mm and in embodiments is about 0.7 mm. The length of the cannula may range from 20 to 35 mm, and in embodiments, is about 30 mm. In embodiments, the cannula is a 23 Ga- or smaller cannula.

Figure 1B:
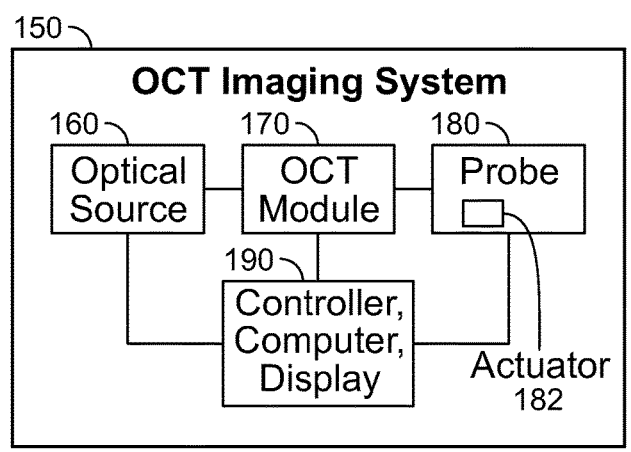
FIG. 1B is a block diagram of an OCT imaging system including a scanning optical probe such as the probe shown in FIG. 1A.

The scanning optical probe can be detachably coupled to an OCT imaging system to produce OCT scans as described herein. With reference to FIG. 1B, an exemplary OCT imaging system 150 is shown including an optical source 160, OCT module 170, a scanning optical probe 180 such as the scanning probe shown in FIG. 1A, and a controller, computer and display 190. The scanning optical probe 180 may be detachably coupled with the OCT system via one or more interlocking connectors, cables, and in embodiments, a flexible umbilical cord (not shown). Additionally, in embodiments, the probe 180 includes an actuator 182 operable to move components of the probe as described herein.

Embodiments of the imaging system 150 split a light generated by the light source 160 into an imaging beam and a reference beam. The imaging beam can be guided to a target region.

The scanning probe 180 collects the imaging light that is reflected off the target region. An OCT module 170 then detects the interference between the reference beam and the returned imaging beam. The OCT module can then create a depth image of the target region based on the detected interference. This depth, or OCT image provides the image of the target region in a range of depth for every point the imaging beam is directed. An OCT image corresponding to a single point on the surface of the target region, such as the surface of the retina 112, is called an A-scan. In imaging systems that scan the imaging beam through a set of target points, the OCT image is typically referred to as a B-scan.

In preferred embodiments described herein, the imaging beam is moved through a set of target points to generate a scan across the target tissue. The scanning operations can be performed under the control of a controller and computer 190 and the results, including the OCT image, can be delivered to a user through, e.g., a display 190.

Figure 2:
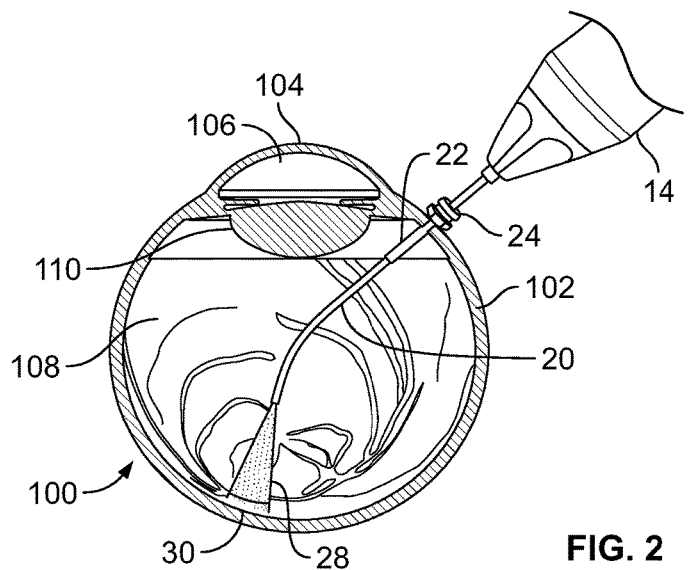
FIG. 2 is an illustration of the scanning optical probe depicted in FIG. 1A in an ophthalmic application.

FIG. 2 illustrates advancing a scanning optical probe into an eye 100 according to some embodiments of the present invention. The eye 100 includes a sclera 102, cornea 104, anterior chamber 106, a posterior chamber 108, and a lens 110 between the chambers. The distal inner surface of the eye 100 supports a retina 30.

The scanning optical probe can be manipulated by a physician using handle 14 to advance cannula 20 into a trocar/valve assembly 22/24, through the sclera 102, and into posterior chamber 108 until the distal region of the cannula is in vicinity of the retina 30. Light 28 is guided to and from the distal end of the cannula 20 as described herein to obtain an OCT scan of the retina. In accordance with embodiments of the invention, various actuating mechanisms disposed within the cannula 20 generate motion for creating the OCT 2-dimensional or B-type scan.

Figure 3:
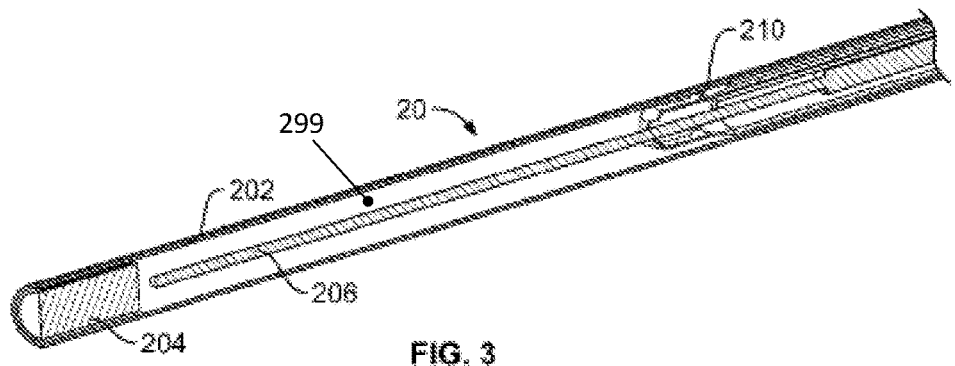
FIG. 3 is a cross sectional view of a distal section of a scanning optical probe in accordance with an embodiment of the present invention.

FIG. 3 depicts an exemplary embodiment of a scanning optical probe 20 having an actuating mechanism for tilting the distal end. The scanning optical probe 20 includes a cannula 202 with a lumen 299 (or passageway through the tube of the cannula 202), lens 204, optical fiber 206, and an actuating mechanism in the form of a tubular-shaped flexible member 210. The flexible member 210, while holding optical fiber 206, is adapted to tilt back and forth (e.g., in a reciprocating motion) thereby creating the desired light beam motion to support OCT image scanning as described herein.

Figure 4:
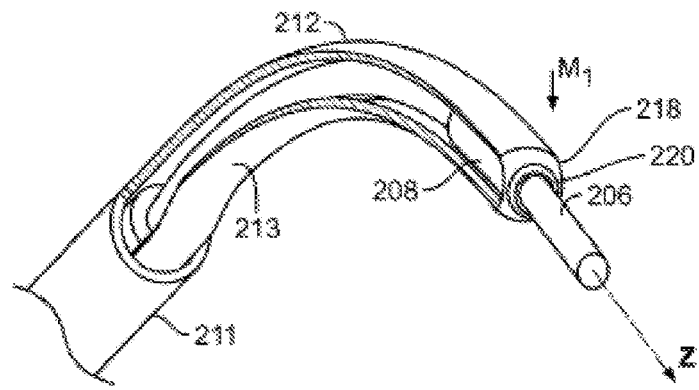
FIG. 4 is a perspective view of a distal section of a scanning optical probe depicted in a flexed orientation.

The actuator mechanism 210 can have various constructs. With reference to FIG. 4, for example, an elongate flexible member includes a tubular body 211, a first arm 212 extending from the body, a second arm 213 opposite the first arm, and a distal face 218 in perpendicular orientation to the axis (Z) of the probe assembly.

Optical fiber 206 can be mounted to the distal face 218 with an adhesive 208 or other suitable bonding agent or process. The face 218 includes an aperture 220 through which optical fiber 206 extends.

The second arm 213 is shown extending into the tubular body 211. In embodiments, the second arm extends through the tubular body and into the handle (not shown). The second arm is axially movable and the body 211 is fixed (e.g., bonded) to an outer cannula (such as, e.g., the cannula 202 shown in FIG. 3). When the second arm 213 is axially retracted relative to body 211, the assembly is deflected in the direction $M_1$. Applying an axially-directed reciprocating motion to arm 213 causes the flexible member and optical fiber to rotate back and forth as desired.

Axially directed reciprocating motion can be applied with an actuator. Non-limiting exemplary actuators include actuators based on pneumatic, electrical solenoid, bimorph piezo strip, voice coil, electrical motor, etc.

Although the embodiment described above in connection with FIG. 4 describes movement of second arm 213 to cause the deflection of the assembly, in other embodiments, second arm 213 is fixed and the body 211 is axially moved causing the desired deflection.

Figure 5:
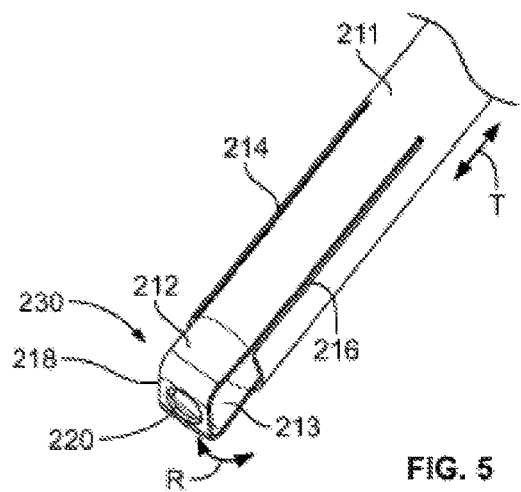
FIG. 5 is a perspective view of a distal section of a component of the scanning optical probe shown in FIG. 3.

FIG. 5 depicts another embodiment of a flexible actuating member 230. The body 211 is axially movable and a tail end of the second arm 213 is immobilized (or otherwise mounted) to the inner wall of a cannula (such as the cannula 202 shown in FIG. 3). Thus, when the body 211 is axially moved (T) relative to the cannula, the head assembly 230 is rotated (R) because the tail end of the strip 213 is immobilized by being bonded to the inner cannula wall. Applying an axially-directed reciprocating motion (T) to body 211 causes the flexible member and optical fiber to rotate (R) back and forth as desired.

The assemblies and components described above can vary widely. In one embodiment, the flexible member 210 is integrally formed from one strip of material. The strip can be shaped by removing material (e.g., machining, or laser cutting) from the tubular shaft 211, thereby defining an elongate free-standing strip and tail between slots 214 and 216. The tail of the strip can be folded back on itself, and into the body 211, thereby defining the first arm 212, second arm 213, and face 220.

Exemplary materials of the flexible support member include steel, alloys, Nitinol, and other materials capable of carrying out the functions described herein. Additionally, the shape of flexible member 210 need not to be tubular. The flexible support member can have a wide variety of shapes. The cross sectional shape of the lumen or passageway extending there through can be, e.g., circular, semi-circular, arcuate, square, U-shaped, L-shaped, or another open-channel or closed shape. Additionally, the lens 204 need not be fixed in the lumen of the cannula 202. In embodiments, a lens is mounted to the optical fiber and the fiber and lens are moveable as an integrated assembly.

FIGS. 6-8 depict another embodiment of a distal section of a scanning optical probe 300 having an actuating mechanism for tilting the distal end. A flexible member 304 is shown extending from cannula 306. The flexible member 304 has a tubular-shaped body and a predefined flexing region comprised of a plurality of slots 305. The slots 305, as described further herein, allow for articulation in a discrete predefined region of the body 304. An optical fiber 310 extends through the tubular body 304, and a lens 312 is fixed or mounted distal to the end of the optical fiber and within the tubular body.

With reference to FIG. 9, the tubular member 304 can be formed from a tube and material is removed in designated areas to form sets of adjacent slots 305 (e.g., by laser cutting or machining). Sets of adjacent slots are shown disposed on diametrically opposing sides of the tubular body. Three adjacent slots are shown in each set, however, the number of adjacent slots per set may vary. In embodiments, a set may have 2-20 adjacent slots, and in some embodiments, a set has greater than 3 adjacent slots.

Additionally, elongated grooves 322, 324 are formed in the tubular body 304 thereby defining a first elongated rod 326. A second elongated rod 336 can be formed diametrically opposite the first rod 326 in the same way that the first elongated rod is formed.

With reference to FIG. 10, elongate rods 326, 336 are shown extending proximally through the tubular body 304 and cannula 306, and into a handle portion 352. The handle portion 352 is shown having an opening 354 to receive a proximal section of the tubular element 304 and cannula 306. Tails or ends of the first and second rods 326, 336 continue into the handle and are coupled to an actuator.

In operation, first rod 326 is moved axially in direction (F) relative to the second rod 336. The second rod 336 follows the first rod either passively or actively in response to the motion. Second rod 336 may be a fixed or moved axially in direction (R) thereby causing the distal tip of the tubular member 304 to tilt towards the second-rod side of the tube 304. Likewise, when the second rod 336 is actuated, the first pull-rod 326 can follow in a passive or active manner, thereby causing the distal tip to tilt towards the first-rod side of the tube.

An example of the distal tip of the flexible member 304 being sequentially moved from a first position (titled/deflected in the direction A), to a second position opposite the first position (titled/deflected in the direction B) by pulling on the first and second rods as described above is illustrated in FIGS. 6-8.

The structures described above (such as, e.g., the rods) can have a wide variety of shapes. Exemplary cross sectional shapes include, without limitation, rectangular, oval, circle, and square, whether hollow or solid, and or other cross sectional shapes. Additionally, the rods and tabs may be integrally formed with the flexing region or bonded thereto.

FIGS. 11-13 depict an embodiment of a distal section of a scanning optical probe 400 having an actuating mechanism for tilting an optical fiber 406 and lens connected thereto 408 relative to a cannula 404. The distal end of the probe is shown having an optional cover 405. Cover 405 can be, e.g., a clear glass window.

The actuator mechanism causes the optical fiber 406 to move by means of a first support member 420 mounted inside the cannula that extends from inside the probe handle (not shown) to the distal end of the cannula 404. The first support member 420 could be, but is not limited to, a tube shape. The first support member 420 has two features (e.g., notches) at the distal end, which form a first guide in the shape of a first tab 422. The first tab 422 is bent inward past the axial centerline of the first support member 420.

The cannula 404 also has notches similar to the notches in first support member 420 except that the notches in the cannula are longer to form a second guide in the form of a second tab 416. The second tab 416 is bent inward past the axial centerline of the cannula. The second tab 416 in the cannula is longer than the first tab 422 and has less spring force than the first tab 422 in the first support member 420. Alternatively, the second tab 416 can be a separate piece and not part of cannula 404.

The first support member 420 is shown disposed inside the cannula 404 and the optical fiber 406 is shown extending through the first support member 420. Similar to embodiments described herein, the proximal end of the first support member (not shown) can be connected to a reciprocating actuator in the probe handle to provide the first support member with axial motion.

When the first support member 420 is in a retracted position (D1) as shown in FIG. 11, the first tab 422 on the first support member 420 is located proximally to the second tab 416 on the cannula 404. The first tab 422 of the first support member 420 pushes the optical fiber 406 down, and the second tab 416 on the cannula (which is located distal to the first tab 422) pushes the fiber up. The contour of the fiber 406 is thus angled in the upward direction.

When the first support member 420 is actuated, the first tab 422 on the first support member 420 is axially advanced to the second tab 416 location on the cannula 404 as shown in FIG. 12, and then further advanced beyond the second tab 416 on the cannula 404 as shown in FIG. 13 corresponding to a displacement of (D2) and (D3) respectively. In embodiments the first tab 422 on the first support member 420 has a greater spring force than the second tab 416 on the cannula. The second tab 416 on the cannula is thus overcome by the force arising from the first tab 422, and the fiber 406 is pushed downward and pointed in a downward direction as shown in FIG. 13.

Although the lens 408 is shown fixed to the end of the optical fiber 406, the invention need not be so limited. In other embodiments the lens is fixed in the cannula and the fiber moves.

Figure 14:
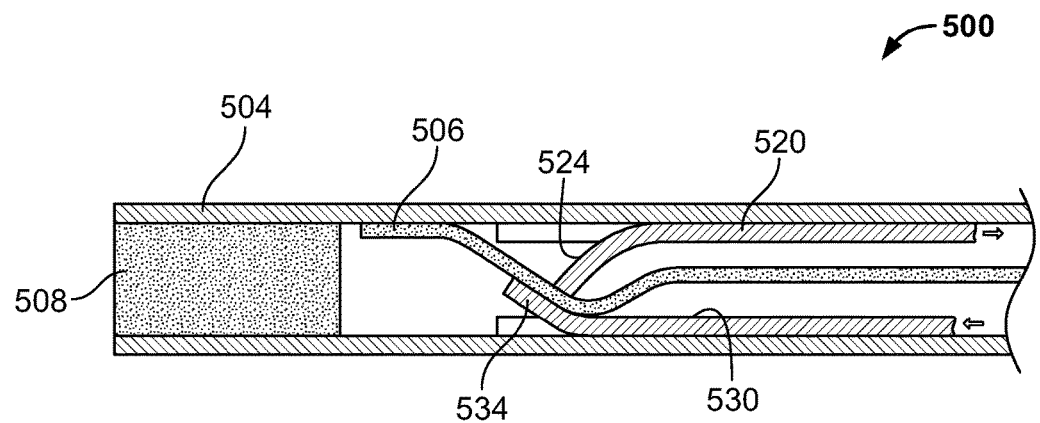
FIGS. 14-15 are cross sectional views of a distal section of another scanning optical probe including various internal optical guide members.

FIG. 14 depicts another embodiment of a distal section of a scanning optical probe 500 having an actuating mechanism for tilting an optical fiber 506 relative to a cannula 504. A first support member 520 is axially movable in the cannula 504. The first support member 520 has a first tab 524 for guiding and biasing optical fiber 506.

A second support member 530 is axially movable in the cannula 504. The second support member 530 has a second tab 534 complimentary to the first tab 524 to bias and guide optical fiber 506 to tilt back and forth within the cannula as described in connection with FIGS. 11-13. Alternately, the second support member 530 can be stationary.

In the embodiment shown in FIG. 14, the support members 520 and 530 can be made from two halves of a tube. Each half would have a complimentary tab as described above. One or both halves are actuated reciprocally from the instrument handle to generate the desired motion. Additionally, the cannula can be a completely intact tubular cannula, namely, smooth and without tabs and slots machined therein.

Figure 15:
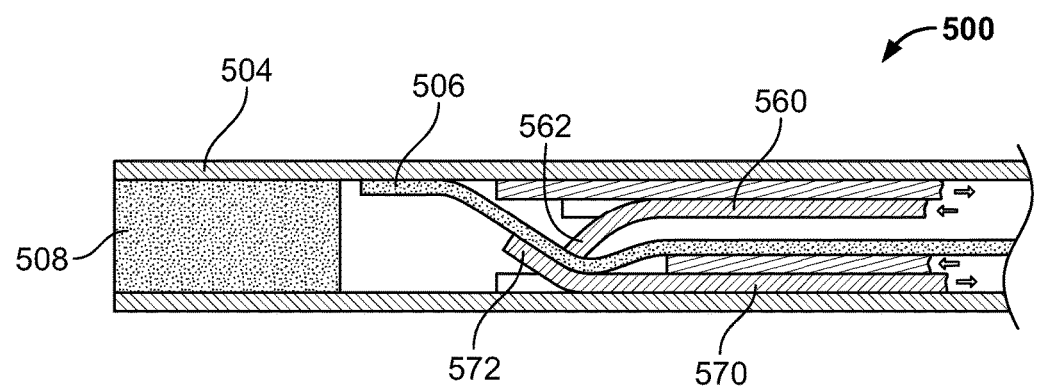

FIG. 15 depicts another embodiment of a distal section of a scanning optical probe 500 having an actuating mechanism for tilting an optical fiber 506 back and forth relative to a cannula 504. The embodiment shown in FIG. 15 is similar to the embodiment described in FIG. 14 except that the support members 560, 570 are two tubes coaxially arranged within the cannula 504. Each support member 560, 570 is axially movable and includes complimentary tabs 562, 572 for guiding and biasing optical fiber 506. Alternatively, the support member 570 can be stationary. One or both tubes are actuated reciprocally to generate the desired movement to the optical fiber 506 as described herein.

Figure 16:
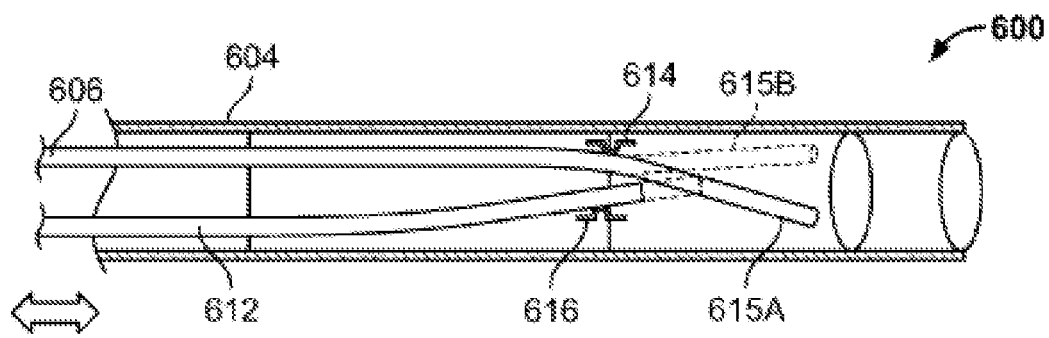
FIG. 16 is a cross sectional view of a distal section of another scanning optical probe including a control member.

FIG. 16 depicts another embodiment of a distal section of a scanning optical probe 600 having an actuating mechanism for tilting an optical fiber 606 back and forth within a cannula 604. An end portion of an elongate control member 612 is advanced distally to push optical fiber 606 from a first position 615A to a second position 615B.

A first guide 614 is shown biasing optical fiber 606 in a first position 615A.

A second guide 616 is shown biasing or guiding the control member 612 in the second direction. Consequently, as the control member is advanced distally the optical fiber is urged upwards. When the control member is retracted, the optical fiber is biased downwards. The control member may be reciprocated at its proximal end similar to the actuating techniques described herein.

Figure 17:
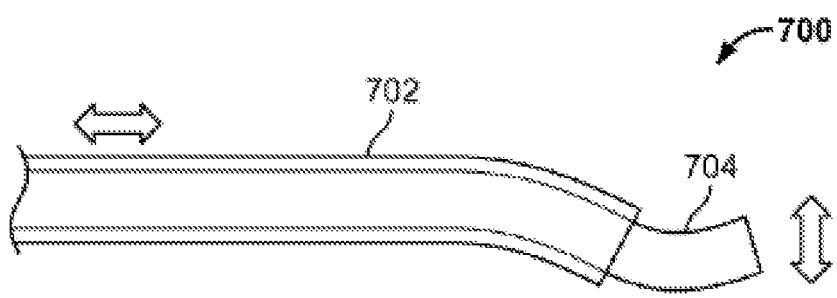
FIGS. 17-18 are side views of a distal section of another scanning optical probe including a pre-shaped sheath.

FIG. 17 depicts another embodiment of a distal section of an actuating mechanism 700 for tilting an optical fiber 704. In the embodiment shown in FIG. 17, optical fiber 704 is biased in a first contour. For example, the optical fiber distal end is pre-shaped with a curve. An outer sheath 702 is shown coaxially surrounding optical fiber. Sheath 702 is shown having a pre-set curve in an opposite direction to optical fiber. When the sheath and fiber are moved relative to one another, the distal end of the optical fiber is deflected back and forth.

Figure 18:
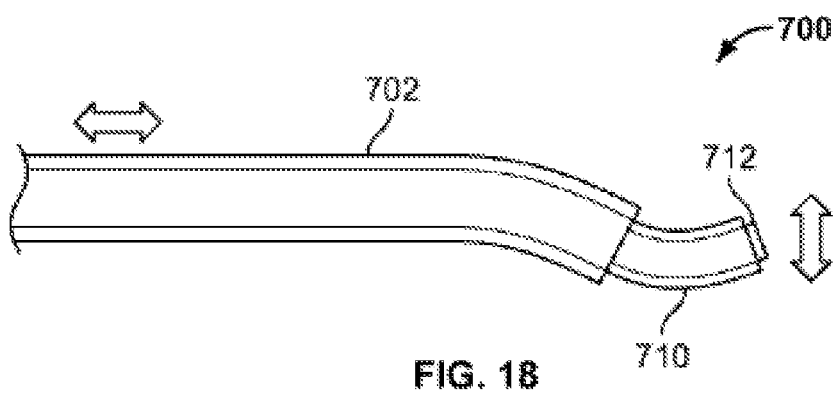

FIG. 18 depicts another embodiment of a distal section of an actuating mechanism 700 for tilting an optical fiber 712 similar to that shown in FIG. 17 except optical fiber 712 is shape-biased in the first position due to biasing guide member 710. The optical fiber 712 is passive and the guide 710 imparts the pre-shape onto the optical fiber. When the sheath 702 and fiber guide assembly are moved relative to one another, the optical fiber tilts back and forth.

The proximal end of the sheath, guide or fiber may be reciprocated by an actuator as described herein. Indeed, there are a wide range of constructs within the scope of the invention to tilt the optical fiber and or lens assembly back and forth within the cannula of a scanning optical probe. Rocking or tilting the optical fiber provides the beam motion for scanning and in particular, for performing OCT scanning of biological tissues.

Figure 19:
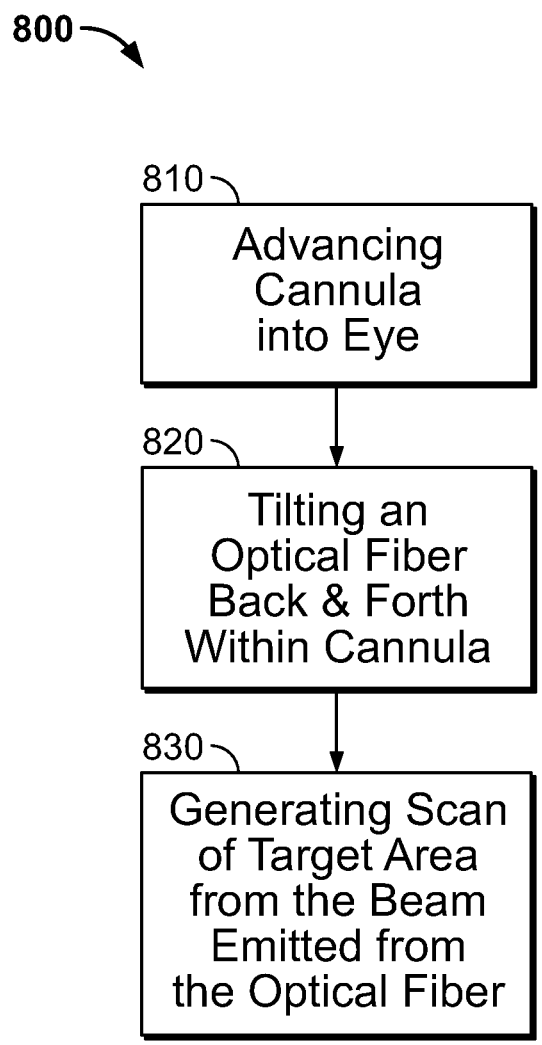
FIG. 19 is a flow chart depicting a method for scanning a target area in accordance with the present invention.

FIG. 19 is an embodiment of a method 800 for scanning a target area of a patient's eye. For simplicity, some steps may be omitted, interleaved, and/or combined. The method 800 is described in the context of using the scanning optical probe 10 to scan the retina of an eye 100 such as that shown in FIG. 2. However, the method 800 can be used in combination with other scanning hand-pieces, and to scan other target structures.

Initially, the scanning optical probe can be removably coupled to an OCT imaging system. Next, and with reference to step 810, a cannula is advanced into the patient's eye. The cannula is preferably advanced through a fluidly sealed trocar cannula assembly such as the trocar cannula assembly 22,24 shown in FIG. 2.

The cannula is advanced until the distal section is in the vicinity of the target tissue to be scanned. In embodiments, the cannula is curved and advanced until the distal section is in the vicinity of the retinal surface.

Step 820 states tilting an optical fiber back and forth within the cannula. Titling the optical fiber may be performed via actuating mechanisms as described herein.

Step 830 states generating a scan of the target area from the beam emitted from the optical fiber. This step can be performed by sending light to, and receiving light reflected from, the target structure. Reflected light is sent back through the probe, and to the OCT system module for processing as described above in connection with FIG. 1B. Additional processing and display of the scanning information may be performed with a processor, computer and display.

In embodiments, the cannula may be repositioned or moved to another target area. Repositioning the end of the distal section of the cannula serves to build a larger scan area of the target structure. Individual scans may be combined on the computer and processor to make larger topographic maps of the target surface.

After the desired steps are completed, the tip of the scanning optical probe, and trocar cannula are removed from the patient's eye.

A scanning optical apparatus, system, and method have been described. The apparatus, system and method have been described in accordance with the exemplary embodiments shown, and one of ordinary skill in the art will readily recognize that there could be variations to the embodiments, and any variations would be within the spirit and scope of invention. Accordingly, many modifications may be made by one of ordinary skill in the art without departing from the spirit and scope of the appended claims.

We claim:

1. A scanning optical probe comprising:
   a cannula comprising a proximal section, distal section, and a lumen extending there through;
   an optical fiber extending through the lumen and into the distal section of the cannula;
   a lens disposed in the distal section of the lumen, and distal to the optical fiber;
   an elongate flexible member disposed within the lumen of the cannula, the elongate flexible member comprising:
   a tubular body;
   a passageway through which the optical fiber extends; and
   a plurality of elongated grooves formed in the elongate flexible member in an axial direction which define a plurality of elongate rods that are axially movable relative to the tubular body; and
   an actuator coupled to the plurality of elongate rods and adapted to provide reciprocating motion to the elongate flexible member in response to the actuator axially moving one or more of the plurality of elongate rods, wherein an end region of the elongate flexible member deflects between a first position and a second position responsive to the reciprocating motion such that light emitted from the optical fiber is directed in a first direction and a second direction corresponding respectively to the first position and the second position of the end region of the elongate flexible member for scanning a target surface in an eye of a patient.

2. The scanning optical probe of claim 1 wherein the tubular body has a central axis extending there through.

3. The scanning optical probe of claim 2 wherein the elongate flexible member further comprises a face disposed in a perpendicular orientation to the central axis of the tubular body, and wherein the optical fiber is attached to the face.

4. The scanning optical probe of claim 2 wherein an end region of the elongate flexible member comprises a first predefined flexing region.

5. The scanning optical probe of claim 4 wherein the first predefined flexing region comprises a set of slots formed in a side wall of the elongate flexible member.

6. The scanning optical probe of claim 5, wherein the plurality of elongate rods are axially moveable relative to the tubular body of the elongate flexible member such that axial movement of each of the plurality of elongate rods cause the end region of the elongate flexible member to deflect at the first predefined flexing region.

7. The scanning optical probe of claim 5 wherein each of the slots has a teardrop shape.

8. The scanning optical probe of claim 7, further comprising a lens disposed in the distal section of the lumen, and distal to the optical fiber, wherein the lens is fixed to the optical fiber.

9. The scanning optical probe of claim 8, wherein the lens is fixed within the lumen of the cannula.

10. The scanning optical probe of claim 1 further comprising a handle wherein said cannula extends distally from the handle.

11. The scanning optical probe of claim 10 wherein the actuator is located within the handle.

12. A scanning optical probe comprising:
a cannula comprising a proximal section, distal section, and a lumen extending there through;
an optical fiber extending through the lumen to the distal section of the cannula;
a lens located at the distal section of the lumen, and distal to the optical fiber;
a first guide located in the lumen of the distal section of the cannula, and biasing the optical fiber to aim in a first direction; and
an elongate control member extending through the lumen and axially movable relative to the first guide to deflect the optical fiber to aim in a second direction; and
a second guide located in the lumen of the distal section of the cannula, and directing the control member in a second direction as the control member is advanced distally to scan a target surface of an eye of a patient.

13. The scanning optical probe of claim 12 wherein the elongate control member is an elongate hollow tube comprising a second guide.

14. The scanning optical probe of claim 13 wherein the first guide is a spring-biased bent tab integral with the cannula.

15. The scanning optical probe of claim 13 further comprising a cylindrical sheath, and wherein the cylindrical sheath comprises the first guide, and wherein said cylindrical sheath is coaxially arranged between the cannula and the control member.

16. A scanning optical probe comprising:
a cannula comprising a proximal section, distal section, and a lumen extending there through;
an optical fiber extending through the lumen to the distal section of the cannula, and biased in a first direction;
a lens located at the distal section of the lumen, and distal to the optical fiber; and
an elongate sheath coaxially surrounding the optical fiber and biased in a second direction substantially away from the first direction of the biased optical fiber, and extending proximally from the distal section of the cannula, and the elongate sheath being axially movable relative to the optical fiber to deflect the optical fiber to aim in a second direction by virtue of the second direction of the biased elongate sheath interacting with the first direction of the biased optical fiber to scan a target surface of an eye of a patient.

17. The scanning optical probe of claim 16 further comprising a biasing tubular member coaxially surrounding the optical fiber and wherein the optical fiber is biased in the first direction based on the biasing tubular member.

* * * * *